United States Patent
Sarkar et al.

(10) Patent No.: US 6,562,572 B1
(45) Date of Patent: May 13, 2003

(54) METHODS FOR AMPLIFYING NUCLEIC ACID SEQUENCES

(75) Inventors: Gobinda Sarkar, Rochester, MN (US); Mark E. Bolander, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/671,043

(22) Filed: Sep. 27, 2000

(51) Int. Cl.[7] .......................... C12Q 1/68; C12P 19/34; C12P 21/06; C07H 19/00; C07H 21/04
(52) U.S. Cl. .................. 435/6; 435/69.1; 435/91.21; 536/22.1; 536/24.33
(58) Field of Search .................. 435/6, 69.1, 91.21; 536/22.1, 24.33

(56) References Cited

U.S. PATENT DOCUMENTS

| | | |
|---|---|---|
| 5,700,644 A | 12/1997 | Gould et al. |
| 5,827,658 A | 10/1998 | Liang |
| 5,882,874 A * | 3/1999 | Fisher ..................... 435/6 |
| 6,124,120 A * | 9/2000 | Lizardi ..................... 435/91.2 |

FOREIGN PATENT DOCUMENTS

WO  WO 91/09124  * 6/1991

OTHER PUBLICATIONS

Hara E et al. Subtractive cDNA cloning using oligo(dT)30–latex and PCR: isolation of cDNA clones specific to undifferentiated human embyonal carcinoma cells. Nucleic Acids Res., 19(25); 7097–7104, 1991.*
Rodriguez IR et al. A novel method for the isolation of tissue–specific genes. Nucleic Acids Res., 20(13): 3528, 1992.*
Lavery DJ et al. Selective amplification via biotin–and restriction–mediated enrichment (SABRE), a novel selective amplification procedure for detection of differentially expressed mRNAs. Proc.Natl.Acad.Sci.USA., 94, 6831–6836, 1997.*
Stratagene Catalog. Gene Characterization kits. Stratagene Catalog. p. 39, 1988.*
DeBouck, *Curr. Opin. Biotechnol.*, 1995, 6(5):597–599.
Edery et al., *Mol. Cell. Biol.*, 1995, 15(6):3363–3371.
Frohman et al., *Proc. Natl. Acad. Sci. USA*, 1988, 85:8998–9002.
Harris et al., *J. Bone Min. Res.*, 1995, 10(2):178–186.
Kang et al., *Proc. Natl. Acad. Sci. USA*, 1998, 95:13788–13793.
Li et al., *Genes Dev.*, 1993, 7(12a):2366–2377.
Liang et al., *Science*, 1992, 257:967–971.
Ralph et al., *Proc. Natl. Acad. Sci. USA*, 1993, 90:10710–10714.
Sagerström et al., *Annu. Rev. Biochem.*, 1997, 66:751–783.
Sanyal et al., *Mol. Biotechnol.*, 1997, 8(2):135–137.
Sarkar et al., *Genomics*, 1990, 6(1):133–143.
Sarkar et al., *PCR: Methods and Applications*, 1993, 2(4):318–322.
Weber et al., *Biotechniques*, 1998, 25(3):415–419.
Weber et al., *Mol. Biotechnol.*, 1998, 9(1):73–77.

* cited by examiner

Primary Examiner—Jeffrey Fredman
Assistant Examiner—Prabha Chunduru
(74) Attorney, Agent, or Firm—Fish & Richardson P.C., P.A.

(57) ABSTRACT

Methods for identifying differentially expressed mRNA molecules are described, as well as methods for amplifying nucleic acid sequences.

23 Claims, 3 Drawing Sheets

Flowchart of SuRF

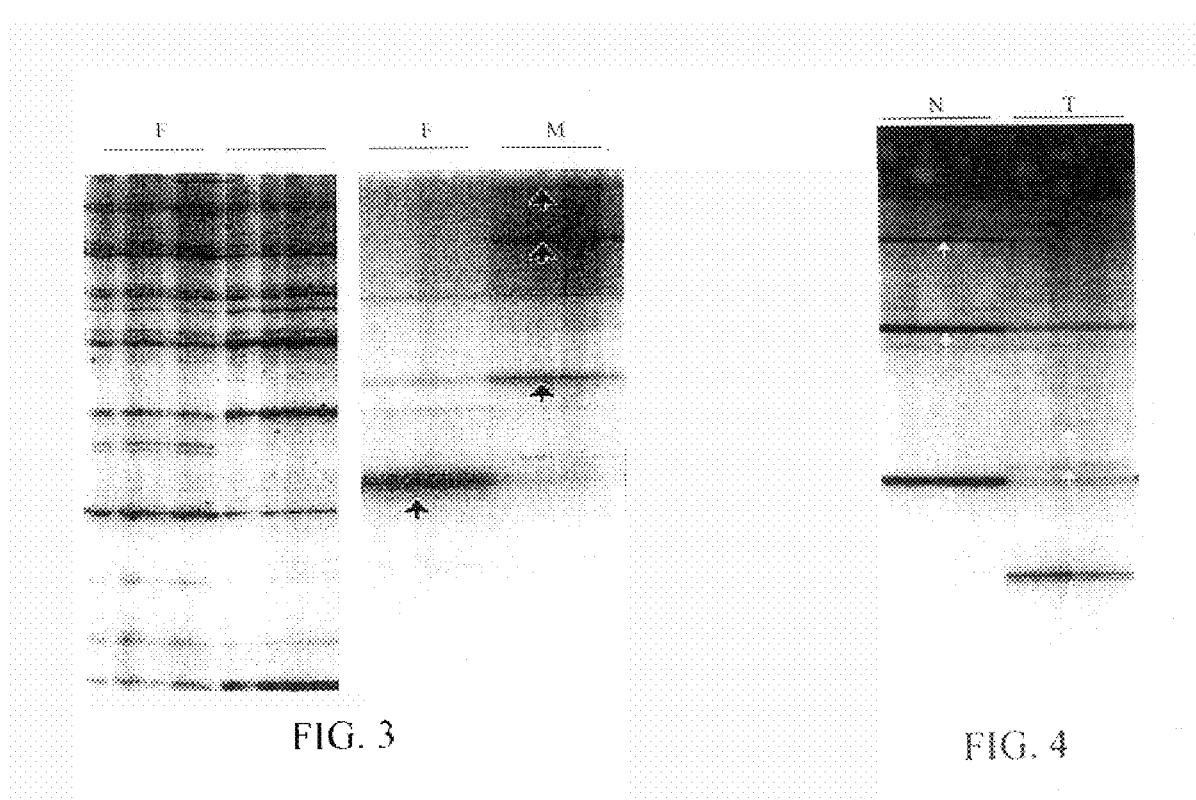
FIG. 3                    FIG. 4

SEQUENCE LISTING

<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: Synthetically generated primers

```
<400> SEQUENCE: 1
ctgccaccca gaagactgtg gat                                          23

<210> SEQ ID NO 2
<211> LENGTH: 23
<212> TYPE: DNA
<213> ORGANISM: Artificial Sequence
<220> FEATURE:
<223> OTHER INFORMATION: Synthetically generated primers

<400> SEQUENCE: 2
cgctgttgaa gtcagaggag acc                                          23

<210> SEQ ID NO 3
<211> LENGTH: 13
<212> TYPE: DNA
<213> ORGANISM: Artificial Sequence
<220> FEATURE:
<223> OTHER INFORMATION: Synthetically generated primers
<221> NAME/KEY: misc_feature
<222> LOCATION: (1)...(13)
<223> OTHER INFORMATION: n = A,T,C or G

<400> SEQUENCE: 3
gaattcnnnt cga                                                     13

<210> SEQ ID NO 4
<211> LENGTH: 13
<212> TYPE: DNA
<213> ORGANISM: Artificial Sequence
<220> FEATURE:
<223> OTHER INFORMATION: Synthetically generated primers
<221> NAME/KEY: misc_feature
<222> LOCATION: (1)...(13)
<223> OTHER INFORMATION: n = A,T,C or G

<400> SEQUENCE: 4
gaattcnnng cgc                                                     13

<210> SEQ ID NO 5
<211> LENGTH: 13
<212> TYPE: DNA
<213> ORGANISM: Artificial Sequence
<220> FEATURE:
<223> OTHER INFORMATION: Synthetically generated primers
<221> NAME/KEY: misc_feature
<222> LOCATION: (1)...(13)
<223> OTHER INFORMATION: n = A,T,C or G

<400> SEQUENCE: 5
gaattcnnng gcc                                                     13

<210> SEQ ID NO 6
<211> LENGTH: 13
<212> TYPE: DNA
<213> ORGANISM: Artificial Sequence
<220> FEATURE:
<223> OTHER INFORMATION: Synthetically generated primers
<221> NAME/KEY: misc_feature
<222> LOCATION: (1)...(13)
<223> OTHER INFORMATION: n = A,T,C or G

<400> SEQUENCE: 6
gaattcnnnc cgg                                                     13

<210> SEQ ID NO 7
<211> LENGTH: 13
```

```
<212> TYPE: DNA
<213> ORGANISM: Artificial Sequence
<220> FEATURE:
<223> OTHER INFORMATION: Synthetically generated primers
<221> NAME/KEY: misc_feature
<222> LOCATION: (1)...(13)
<223> OTHER INFORMATION: n = A,T,C or G

<400> SEQUENCE: 7
ggatccnnna tga                                                              13

<210> SEQ ID NO 8
<211> LENGTH: 13
<212> TYPE: DNA
<213> ORGANISM: Artificial Sequence
<220> FEATURE:
<223> OTHER INFORMATION: Synthetically generated primers
<221> NAME/KEY: misc_feature
<222> LOCATION: (1)...(13)
<223> OTHER INFORMATION: n = A,T,C or G

<400> SEQUENCE: 8
ggatccnnna tgt                                                              13

<210> SEQ ID NO 9
<211> LENGTH: 13
<212> TYPE: DNA
<213> ORGANISM: Artificial Sequence
<220> FEATURE:
<223> OTHER INFORMATION: Synthetically generated primers
<221> NAME/KEY: misc_feature
<222> LOCATION: (1)...(13)
<223> OTHER INFORMATION: n = A,T,C or G

<400> SEQUENCE: 9
ggatccnnna tgg                                                              13

<210> SEQ ID NO 10
<211> LENGTH: 13
<212> TYPE: DNA
<213> ORGANISM: Artificial Sequence
<220> FEATURE:
<223> OTHER INFORMATION: Synthetically generated primers
<221> NAME/KEY: misc_feature
<222> LOCATION: (1)...(13)
<223> OTHER INFORMATION: n = A,T,C or G

<400> SEQUENCE: 10
ggatccnnna tgc                                                              13
```

METHODS FOR AMPLIFYING NUCLEIC ACID SEQUENCES

TECHNICAL FIELD

This invention relates to methods for amplifying nucleic acid sequences and for identifying differentially expressed genes.

BACKGROUND

Changes in the level of gene expression are important indicators for differentiation and development including abnormal cell physiology and neoplasia. Thus identification and characterization of differentially expressed genes has important implications for understanding the molecular mechanisms of growth, differentiation, and development. Since cancer is primarily a result of abnormal differentiation, identification of genes associated with a given cancer can provide important clues to its diagnosis and prognosis, and may even help identify target(s) for therapy.

SUMMARY

The need for a simple and effective method to rapidly identify coding sequences continues to exist even though the complete genome of many organisms, including humans, is or will soon be available. Availability of genomic sequence does not provide instant information on all potential coding regions and does not allow tissue-specific or cell-specific genes to be readily identified. Thus, the invention is based on methods that can be used to rapidly identify coding sequences and differentially expressed genes.

In particular, the invention features methods for amplifying nucleic acid sequences and methods for collecting subtracted RNA molecules. Amplification methods of the invention allow sequences from both prokaryotic and eukaryotic organisms to be identified, (e.g., coding sequences) as the method is not dependent on the existence of a poly A tail on a messenger RNA (mRNA). Collection of subtracted RNAs allows common RNAs to be removed before further processing, reducing identification of redundant genes and increasing the chance of identifying rare, differentially expressed genes. Subtracted RNA samples can provide a template for obtaining a population of complementary DNA (cDNA) molecules that can be identified by various techniques, including the amplification method of the present invention.

In one aspect, the invention features a method of amplifying nucleic acid sequences. The method includes amplifying a population of cDNA molecules using at least one nucleic acid primer pair (e.g., at least 4, 8, 16, 32, or 64 primer pairs), with each primer pair consisting of nucleic acid primers 10 to 40 nucleotides in length, wherein a first nucleic acid primer of the primer pair comprises, in 5' to 3' orientation, a restriction endonuclease recognition sequence and a translation initiation codon, and wherein a second nucleic acid primer of the primer pair comprises two restriction endonuclease recognition sequences. The population of cDNA molecules can be from a biological sample, e.g., prokaryotic cells, eukaryotic cells, neoplastic cells, or a tissue sample. The first nucleic acid primer can include the sequence 5'-R-S-ATG-N-3', where R represents a restriction endonuclease recognition sequence, S represents a degenerate nucleotide sequence from 1 to 10 nucleotides in length, and N represents an A, C, G, or T nucleotide. The second nucleic acid primer can include the sequence 5'-$R_1$-S-$R_2$-3', where $R_1$ and $R_2$ are the same or different restriction endonuclease recognition sequences and S is a degenerate nucleotide sequence from 1 to 10 nucleotides in length.

The invention also features a composition that includes a plurality of different nucleic acid molecules, wherein each nucleic acid molecule includes the sequence 5'-R-S-ATG-N-3', where R represents a restriction endonuclease recognition sequence, S represents a degenerate nucleotide sequence from 1 to 10 nucleotides in length, and N represents an A, C, G, or T nucleotide, and wherein each nucleic acid molecule is 10 to 40 nucleotides in length.

In another aspect, the invention features a kit that includes an initiation nucleic acid primer and a double restriction site nucleic acid primer (DRSP), wherein each primer is 10 to 40 nucleotides in length, wherein the initiation nucleic acid primer has the sequence 5'-R-S-ATG-N-3', where R represents a restriction endonuclease recognition sequence, S represents a degenerate nucleotide sequence from 1 to 10 nucleotides in length, and N represents an A, C, G, or T nucleotide, and wherein the double restriction site nucleic acid primer includes at least two restriction endonuclease recognition sequences.

The kit can include a plurality of different initiation nucleic acid primers (e.g., at least four or at least 16 different initiation nucleic acid primers). The at least four different initiation nucleic acid primers can have the sequences 5'-R-S-ATG-A-3', 5'-R-S-ATG-C-3', 5'-R-S-ATG-G-3', and 5'-R-S-ATG-T-3', where R represents a restriction endonuclease recognition sequence and S represents a degenerate nucleotide sequence from 1 to 10 nucleotides in length.

The kit further can include a plurality of different double restriction-site nucleic acid primers (e.g., at least four or at least 16 different double restriction-site primers), wherein each double restriction site nucleic acid primer includes two restriction endonuclease recognition sequences. The kit also can include a sorting element such as an oligo-dT magnetic bead, an oligo-dT biotin molecule, or an oligo-dT cellulose molecule.

The invention also features a method of collecting differentially expressed mRNA molecules. The method includes hybridizing a population of mRNA-derived cDNA molecules from a first sample to a population of RNA molecules from a second sample; and collecting unhybridized, differentially expressed RNA molecules. The mRNA-derived cDNA molecules can be coupled to a sorting element such as an oligo-dT magnetic bead, an oligo-dT biotin molecule, or an oligo-dT cellulose molecule. The first or the second sample can be a tissue sample, prokaryotic cells, eukaryotic cells, or neoplastic cells.

In yet another aspect, the invention features a method of identifying differentially expressed mRNA molecules. The method includes hybridizing a population of mRNA-derived cDNA molecules from a first sample to a population of RNA molecules from a second sample; converting unhybridized, differentially expressed RNA molecules to subtracted cDNA molecules; and identifying the subtracted cDNA molecules, wherein the subtracted cDNA molecules correspond to differentially expressed mRNA molecules.

The identifying step can include amplifying the subtracted cDNA molecules to form amplified cDNA molecules. The subtracted cDNA molecules can be amplified using a plurality of primer pairs, wherein each primer pair includes an initiation nucleic acid primer and a double restriction site primer, wherein the initiation nucleic acid primer has the general sequence 5'-R-S-ATG-N-3', where R represents a restriction endonuclease recognition sequence, S represents a degenerate nucleotide sequence from 1 to 10 nucleotides in length, and N represents an A, C, G, or T nucleotide, and wherein the double restriction site nucleic acid primer includes two restriction endonuclease recognition sequences. The identifying step further can include sequencing the amplified cDNA molecules. The amplified cDNA molecules can be detectably labeled with a radioisotope or a non-radioactive label (e.g., a fluorescent moiety). A non-radioactive dye also can be used to detect the amplified cDNA molecules.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 3 is an autoradiogram of differentially expressed sequences identified by subtracted RNA fingerprinting. Left panel—conventional differential display pattern between RNAs from FOB (F) and MG63 (M) cells. Right panel—SuRF pattern of the above RNA samples with the same set of primers. Upward arrows in the right panel indicate potential differentially expressed sequences identified by SuRF.

FIG. 4 is an autoradiogram of amplification results between FOB(N) and MG63(T) cell RNAs. Potential differentially expressed bands are indicated by upward arrows.

DETAILED DESCRIPTION

Figure 1:
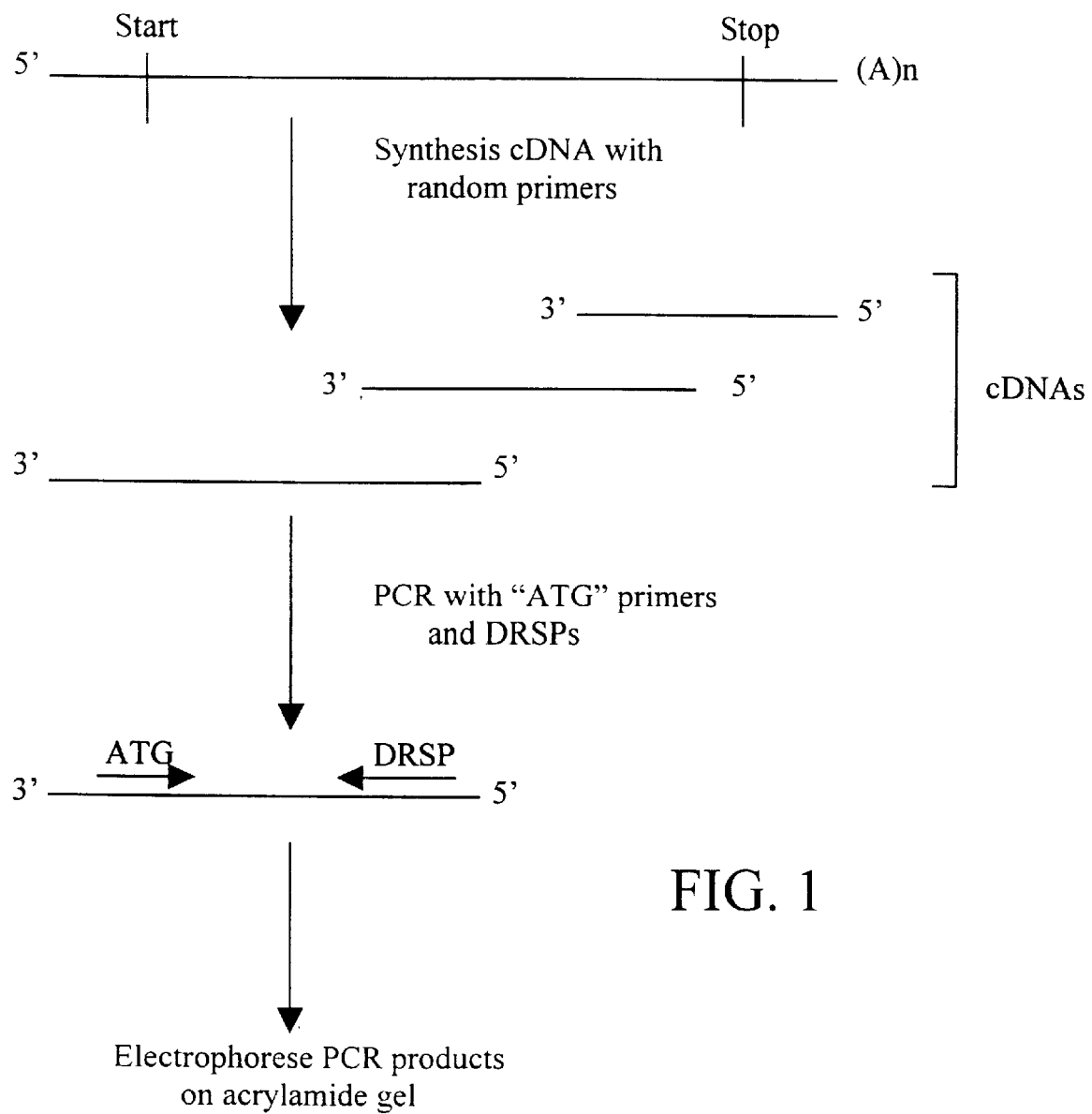
FIG. 1 is a schematic of the method for preferentially amplifying coding sequences (PACS). The arrow with "ATG" on top and the arrow with "DRSP" on top represent forward and reverse primers, respectively.

Methods of the invention allow expressed sequences to be readily identified, including genes that are up-regulated, genes that are down-regulated, and genes that are differentially expressed. Functional regions of mRNAs (i.e., the coding regions) are preferentially amplified in one method of the invention. The term "preferential" indicates that coding regions are amplified more frequently than non-coding regions. In general, the method includes amplifying a population of cDNA molecules with at least one nucleic acid primer pair that includes an initiation primer and a DRSP. FIG. 1 provides a schematic of a "preferential amplification of coding sequences" (PACS) method of the invention. As the initiation codon of most organisms is ATG, the method can be used to identify expressed sequences from almost all organisms. The initiation codon ATG also is not highly repetitive in open reading frames, diminishing the probability of generating very small sequences or multiple sequences from the same region of an mRNA.

Figure 2:
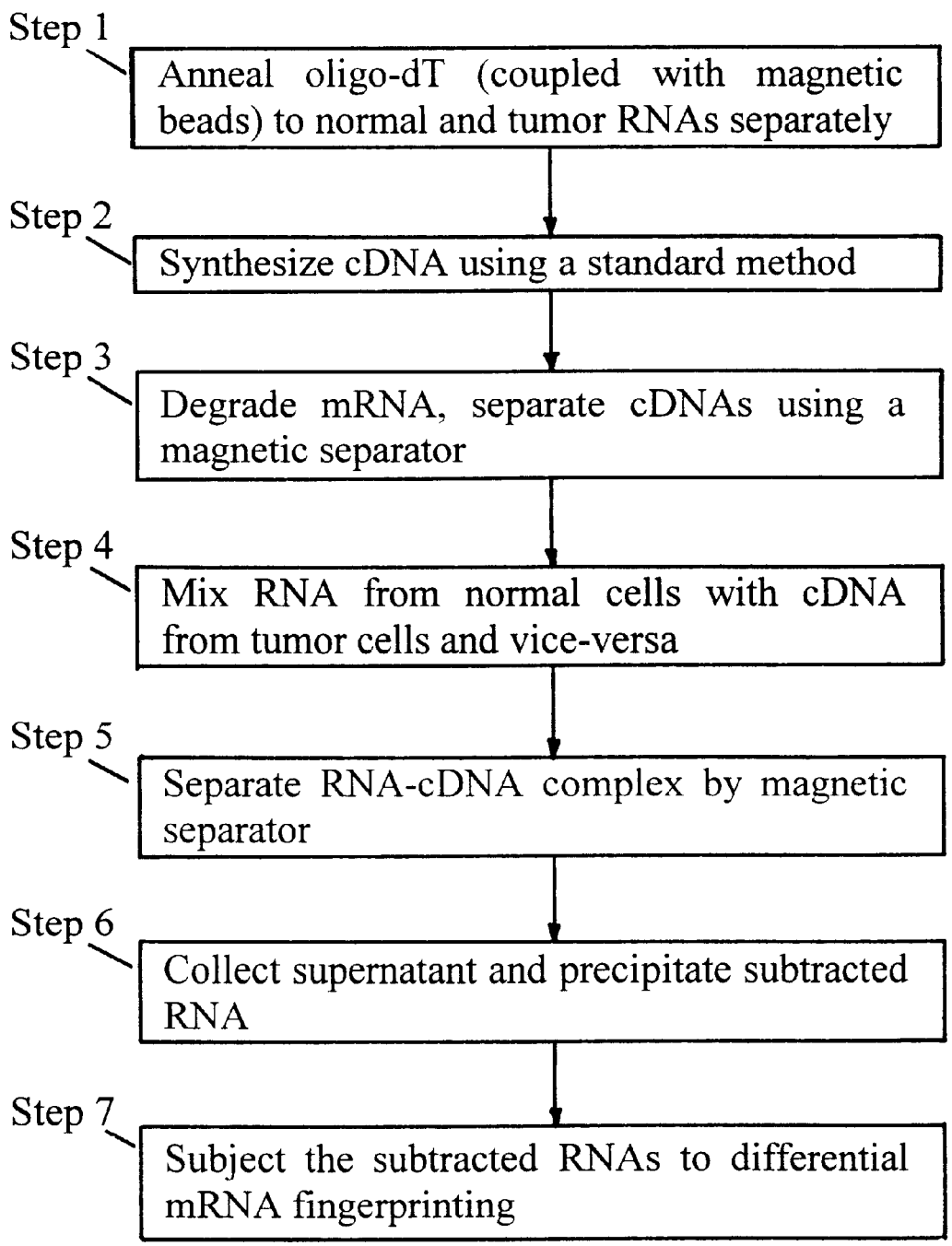
FIG. 2 is a schematic of the method for subtracted RNA fingerprinting.

The invention also provides methods for producing subtracted RNA samples, which eliminates common mRNAs between two samples. See FIG. 2 for a schematic of the method for obtaining subtracted RNA samples. Subtracted RNA samples can be used as templates for obtaining populations of cDNA molecules that are differentially expressed between two samples or that are tissue specific. Such cDNAs can be analyzed using standard differential display techniques, including, for example, differential display PCR (ddPCR) or arbitrarily primed PCR, or can be analyzed by the subtracted RNA fingerprinting (SuRF) method or PACS method described herein. For SuRF, subtracted RNA samples are converted to populations of cDNAs, which are amplified with at least one nucleic acid primer pair and analyzed. One advantage of the SuRF method of the invention is that the method can be applied directly to RNA, eliminating the need to generate multiple cDNA libraries. In either case, after amplification of differentially expressed genes, amplified products can be separated by electrophoresis and can be sequenced. Populations of cDNA molecules obtained from subtracted RNA samples also can be used to produce microarrays in which the cDNA molecules are attached to a solid substrate in discrete locations.

Nucleic Acid Primers

To preferentially amplify coding sequences, at least one pair of nucleic acid primers is used, with each primer approximately 10 to 40 nucleotides in length (e.g., 13–18 nucleotides). Nucleic acid primers can be synthesized using known methodologies, including automated DNA synthesis in the 3' to 5' direction using phosphoramidite technology. Each primer pair includes an initiation primer and a DSRP.

An initiation primer of the invention contains, in 5' to 3' orientation, a restriction endonuclease recognition sequence and a translation initiation codon. More specifically, the initiation primer can include the sequence 5'-R-S-ATG-N-3', where R represents a restriction endonuclease recognition sequence, S represents a degenerate nucleotide sequence from one to 10 nucleotides in length, and N represents an A, C, G, or T nucleotide. The restriction endonuclease recognition sequence can be that of any known restriction enzyme, including, for example, the recognition sequences of EcoRI, BamHI, PstI, BglII, or HindIII, restriction endonucleases. Typically, the degenerate nucleotide sequence is three nucleotides in length. A "degenerate nucleotide sequence" refers to a nucleotide sequence in which two or more different nucleotides are present at the same position in different primers. Because of this degeneracy, each initiation primer of a given sequence actually contains multiple initiation primers. Preferably, the degenerate sequence is completely degenerate, i.e., an A, C, G, and T each are present at the same position of different primers. For example, the sequence 5'-R-S-ATG-A-3', where S is three completely degenerate nucleotides, represents 64 different initiation primers.

DRSPs contain at least two restriction endonuclease recognition sequences. Typically, a DRSP has the sequence 5'-$R_1$-S-$R_2$-3', where $R_1$ and $R_2$ are the same or different restriction endonuclease recognition sequences and S is a degenerate nucleotide sequence from one to 10 nucleotides in length. The restriction endonuclease recognition sequences can be that of any known restriction enzyme, as discussed above, although for $R_2$, restriction endonuclease recognition sequences of four base cutters typically are used. Non-limiting examples of restriction endonucleases that recognize a four nucleotide sequence (or a four nucleotide core sequence) include CfoI, MspI, HaeIII, HpaII, BstI, MseI, AatII, and BstUI.

Populations of cDNA Molecules

A population of cDNA molecules typically is used as a template for amplifying coding sequences. Populations of cDNA molecules can be obtained by standard methodology and can be obtained from any biological sample, including eukaryotic cells (e.g., plant, human, or neoplastic cells), prokaryotic cells, and tissue samples (e.g., breast or prostate cancer biopsy material). Typically, total RNA is extracted from cells or tissue. In eukaryotic samples, poly(A)$^+$RNA is isolated from the total RNA using oligo(dT) and converted to a population of cDNAs using random primers and reverse-transcriptase. Total RNA can be isolated from a biological sample using reagents such as guanidinium or phenol and SDS. See, *Short Protocols in Molecular Biology*, Ed. by Ausubel et al., Greene Publishing Associates and John Wiley & Sons (1992) Page 4–1 to 4–13. For example, a monophasic reagent that includes phenol, isoamyl alcohol, guanidinium isothiocyanate, and β-mercaptoethanol (PIG-B) can be used to extract total RNA. See, Weber et al., *Mol. Biotechnol.* (1998) 9(1):73–77, for a description of the PIG-B procedure. There also are many commercially available kits that can be used for extracting total RNA (e.g., a RNA isolation kit from Fluka (St. Louis, Mo.) or AquaPure RNA isolation kit from BioRad (Hercules, Calif.)). Purified total RNA also is commercially available. See, for example, Premium RNA™ Products from Clontech (Palo Alto, Calif.).

Alternatively, populations of cDNA molecules can be obtained from subtracted RNA samples. A useful method for obtaining subtracted RNA samples is described herein (see, e.g., FIG. 2). In this method, mRNAs (poly(A)$^+$RNAs) are independently isolated from two or more samples of total RNA using a sorting element. A "sorting element" refers to a compound that can be used to tag a nucleic acid molecule. Typically, a sorting element contains an element that recognizes the nucleic acid molecule (e.g., can hybridize to a region of the nucleic acid, such as oligo(dT)) and an element that can be used to isolate the nucleic acid molecule (e.g., magnetic beads, biotin, or cellulose). If the sorting element is oligo(dT) coupled to a magnetic bead, a magnetic separator can be used to isolate the tagged nucleic acid molecules (e.g., poly(A)$^+$RNA). If oligo(dT) is coupled to biotin, avidin can be used to isolate the tagged nucleic acid molecules.

After poly(A)$^+$RNAs are obtained from each sample, cDNAs are synthesized based on each population of poly(A)$^+$RNA. The poly(A)$^+$RNAs can be degraded and the single-stranded cDNAs from each sample can be isolated using the sorting element. To obtain subtracted RNAs, cDNAs from one sample are mixed with total RNA or poly(A)$^+$RNA from the second sample and vice versa, and each mixture is allowed to hybridize under high stringency conditions. As used herein, "high stringency conditions" includes temperatures of 60 to 75° C. and 0.3 to 0.6M NaCl. A particularly useful binding buffer contains 20 mM Tris-HCl, pH 8.0 and 0.5M NaCl. After hybridization of the cDNAs and total RNA or poly(A)$^+$RNA, unhybridized RNAs (i.e., the subtracted RNA) are collected. The sorting element attached to the cDNAs can be used to facilitate this process, e.g., a magnetic separator can be used to pellet the hybridized RNA and cDNA molecules and the subtracted RNA molecules are obtained from the supernatant.

The ratio of the amount of total RNA or poly(A)$^+$RNA from the sample from which it is desired to remove common RNAs (tester RNA) to the initial RNA sample that is converted to cDNAs (competing RNA) can be varied. For example, the ratio of tester RNA to competing RNA can be 1:1 to 1:6. Similar results have been observed with ratios of tester RNA to competing RNA of 1:1, 1:3, and 1:4.

Preferential Amplification of Coding Sequences

Coding sequences are preferentially amplified using polymerase chain reaction (PCR) techniques and the initiation primers and DRSPs described above. General PCR techniques are described, for example in PCR Primer: A Laboratory Manual, Ed. by Dieffenbach, C. and Dveksler, G., Cold Spring Harbor Laboratory Press, 1995. Typically, 30 to 48 cycles of PCR are performed on a population of cDNA molecules in a suitable buffer with about 5–15 pmol of each PCR primer, deoxynucleotides (dNTPs), DNA polymerase, and salt (e.g., 1 to 3 mM MgCl$_2$ and 0 to 150 mM KCl). To facilitate detection of amplified products, a detectably labeled nucleotide can be included in the amplification reaction mixture such that it is enzymatically incorporated into the amplified product during extension. The nucleotide can be radioactively labeled with an isotope such as $^{32}$P or $^{35}$S, or can be non-radioactively labeled with a fluorescent nucleotide derivative such as ChromaTide™ (Molecular Probes, Inc., Eugene, Oreg.).

For differential display, PCR is performed independently on two populations of cDNA molecules (e.g., a population of cDNAs obtained from a neoplastic cell and a population of cDNAs obtained from a normal cell, or populations of cDNAs obtained from subtracted RNA samples) and the amplification products are compared. For example, the amplification products can be electrophoresed through denaturing polyacrylamide gels (e.g., 6% polyacrylamide containing 8M urea), and the pattern of the amplification products can be examined for each sample, i.e., it can be noted which amplification products are present or absent in each sample.

To increase the number of coding sequences that are amplified, multiple primer pairs can be used (e.g., 4, 8, 16, 32, or 64 primer pairs). Based on results described herein, it is estimated that each pair of primers produces approximately 125 amplified nucleic acid molecules, excluding approximately 75 small, amplified products. Thus, if sixteen different combinations of primers are used (four initiation primers and four DRSPs), it is equivalent to screening ~2,000 different mRNAs and equivalent to about 15% of all the expressed genes in a given cell (assuming a cell expresses ~15,000 genes). If 64 different combinations of primers are used (four initiation primers and sixteen DRSPs), it estimated that ~100% of the expressed genes in a given cell can be amplified.

Subtracted RNA Fingerprinting

Subtracted RNA samples can be analyzed by the SuRF method of the invention. For example, subtracted RNAs can be converted to cDNAs using an oligo(dT) primer. PCR can be performed as described above for the PACS method, using, for example, primer pairs that include an oligo(dT) primer and a DRSP. The oligo(dT) primer can include an A, C, or G nucleotide at the 3', e.g. $T_{20}A$, $T_{20}G$, and/or $T_{20}C$. The population of amplified products can be analyzed as described above.

Articles of Manufacture

Nucleic acid primers described herein can be combined with packaging material and sold as an article of manufacture (e.g., a kit). Components and methods for producing articles of manufacture are well known. The articles of manufacture include an initiation primer of the invention and further can include a DRSP. For example, the kit can include four or more initiation primers and four or more DRSPs (e.g, 16 DRSPs). In addition, kits further can contain reagents for amplifying products or for detecting analytes, including, for example, nucleotides, DNA polymerase, oligo-dT, or a sorting element such as oligo-dT coupled to magnetic beads, biotin, or a cellulose molecule. Instructions describing how the nucleic acid primers can be used to identify differentially expressed genes may be included in such kits.

The invention will be further described in the following examples, which do not limit the scope of the invention described in the claims.

EXAMPLES

Example 1

Materials and Methods

Isolation of RNA from Cultured Cells—Total RNA was isolated from cultured FOB cells, a reference normal osteoblast cell line (Harris et al., *J. Bone Min. Res.*, 10:178–186 (1995)) and cultured MG63 cells, a human parosteal osteosarcoma cell line, by the PIG-B procedure (Weber et al., *Mol. Biotech.*, 9:73–77 (1998)). RNA samples were treated with DNase to destroy contaminating genomic DNA, then quantitated by measuring absorption in a UV-spectrometer. The integrity of the RNA samples was evaluated by electrophoresis through a 1% agarose gel.

Mutually Subtracted RNA Fingerprinting (SuRF)—Oligo-dT coupled magnetic beads (Perceptive Biosystems, Framingham, Mass.) (100 µl) were washed, then resuspended in 100 µl of binding buffer according to a protocol supplied by the manufacturer DEPC-treated water was added to 15 µg of total RNA for a total volume of 90 µl, which then was incubated at 65° C. for five minutes before adding 10 µl of 5M NaCl. To this RNA, 25 µl of washed oligo-dT coupled magnetic beads were added, mixed by vortexing, microfuged for five seconds, and left at room temperature for five minutes. The RNA-oligo-dT mix was pelleted with a magnetic separator (supplied by Perceptive Biosystems), and the supernatant, which contains mostly ribosomal and transfer RNAs, was aspirated and discarded. The pellet of RNA-oligo-dT complex was washed three more times with the wash buffer and the pellet saved for cDNA synthesis.

cDNA synthesis was performed in a final volume of 20 µl containing 2 µl of 20 mM dNTP, 20 units of RNase inhibitor (RNAsin), 3 µl (21 units) of AMV-RT, 10 µl water, and the RNA-oligo-dT complex. Reverse transcriptase was added last to the reaction mix. Incubation was at 37° C. for one hour, after which 2 µl of 0.5 M EDTA (pH 8.0) were added to stop the enzymatic reaction.

To degrade the RNA portion of the RNA-cDNA hybrid, 25 µl of 150 mM NaOH were added to the above reaction, followed by 25 µL each of 1.0 M Tris-Cl (pH 8.0) and 1.0 N HCl. The mixture was vortexed and incubated at room temperature for 15 minutes. The cDNA was recovered as a pellet using the magnetic separator, washed with 250 µl of TE, pH 8.0 (10 mM Tris-Cl+1 mM EDTA), vortexed, and placed on magnetic separator to recover the cDNA. This procedure was repeated five more times.

The pellet from the above step was resuspended in 50 µl of binding buffer by pipeting up and down to mix, and 5 µg of total RNA from a desired source from which common mRNAs need to be removed was added. This RNA-cDNA mix was incubated at 65° C. for ten minutes, followed by 1 h at room temperature, then placed in a magnetic separator and the supernatant containing the subtracted RNA was collected. RNA was precipitated by adding 5 µl of 10 mg/ml glycogen and 125 µl of absolute alcohol and storing at −20° C. overnight. RNA was recovered by centrifugation in a microfuge (Eppendorf) for 30 minutes in the cold room and the supernatant was discarded. After the RNA pellet was air-dried, the RNA was converted to cDNA with oligo-dT (without magnetic beads) using a standard protocol. See, Sarkar et al., *Genomics*, 6:133–143 (1990).

For differential display, PCR was carried out in 20 µl reactions using different primer combinations with 45 cycles of extension at 94° C. for one minute, annealing at 40° C. for two minutes, and extension at 72° C. for one minute. PCR reactions contained 0.2 µl of $\alpha$-$^{32}$P-dCTP(10 mCi/mmol). Reactions were stopped with 20 µl of a stop buffer containing 90% formamide, 2 mM EDTA, 0.25% of Xylene cyanol, and 0.25% bromophenol blue. A portion of the reaction (3 µl) was denatured at 90° C. for ten minutes and electrophoresed on a 6% polyacrylamide gel containing 8 M Urea. After electrophoresis, the gel was dried and subjected to autoradiography.

Extraction, cloning and sequencing of DNA from gel slices—DNA from dried gel slices was extracted by adding 100 µl of $H_2O$ to the dried gel strip, removing the backing paper, boiling for ten minutes, then incubating at 37° C. overnight. The tube containing the slurry was microfuged for 25 minutes at maximum speed, and the aqueous portion was transferred to a fresh eppendorf tube. DNA was precipitated with 5 µl of 10 mg/ml glycogen, 10 µl of 3 M sodium acetate (pH 5.0), and 200 µl of absolute alcohol at −20° C. overnight, followed by microfugation for 30 min at maximum speed at 4° C. The resulting pellet was air dried and dissolved in 10 µl water. One µl of this DNA was reamplified by PCR before cloning (using pGemT cloning kit from Promega Corporation) and sequencing. The sequences were evaluated through FastA or Blastsearch programs.

Semi-quantitative Reverse Transcriptase Polymerase Chain Reaction (RT-PCR) Semi-quantitative RT-PCR was carried out in a total volume of 20 µl containing 10 mM Tris-Cl, pH 8.3, 200 µm dNTPs, 1.5 mM $MgCl_2$, 2 pmol of each primer (primer pairs for a test mRNA and GAPDH (glyceraldehyde acid phosphate dehydrogenase) mRNA were included), 0.5 of Amplitaq, and 1 µl of randomly primed cDNA. Primers used for GAPDH mRNA were: 5'CTGCCACCCAGAAGACTGTGGAT3' (SEQ ID NO:1) and 5'CGCTGTTGAAGTCAGAGGAGACC3' (SEQ ID NO:2). After denaturation at 94° C. for five minutes, 35 cycles of PCR typically were performed with the cycling profile set for denaturation at 94° C. for one minute, annealing at 65° C. for one minute, and extension at 72° C. for one minute. A portion of the reaction (5 µl) was electrophoresed on a 2% agarose gel, and the amplified DNA was visualized by staining with ethidium bromide.

PACS Methodology—cDNAs produced from total RNA of osteoblast or osteosarcoma cells were subjected to PCR as follows: 1 ml of the cDNA was mixed with 10 pmol of each PCR primer in a final volume of 20 ml containing 10 mM Tri-HCl pH 8.3, 1.5 mM $MgCl_2$, 2 mM dNTP, 100 mM KCl, and 5 mCi of $\alpha$-$^{32}$P-dCTP (10 mCi/mmol). Forty-five cycles of PCR were performed at 94° C. for 1 minute, 40° C. for 2 minutes, and 72° C. for 1 minute. PCR reactions were stopped by adding 20 µl of a stop buffer containing 90% formamide, 2 mM EDTA, 0.25% bromophenol blue, and 0.25% of Xylene cyanol. Three µl of this PCR product was denatured at 90° C. for five to ten minutes and electrophoresed through a 6% polyacrylamide gel containing 8 M Urea. The gel was dried after electrophoresis and subjected to autoradiography.

Northern blotting: Total cellular RNAs (10 µg) were electrophoresed through 0.8% formaldehyde-agarose gels.

After transfer to a membrane, the Northern blots were hybridized overnight with PCR generated radioactive probes at 42° C., followed by standard washing with SSC and SDS. The final wash was with 0.1%SSC+0.1% SDS at 65° C. for 30 mm.

Example 2

Identification of Differentially Expressed mRNAs Between Cultured Osteoblasts and Osteosarcoma Cells by SuRF Potential osteosarcoma-associated genes were identified using SuRF between an immortalized normal human cell line and a human parosteal osteosarcoma cell line. To anchor the poly A region of mRNAs during PCR, $T_{20}A$, $T_{20}G$, and $T_{20}C$ primers were used. The general structure of the other (random) primers was as follows: 5'-EcoR1 restriction site sequence -NNN- a four-base restriction site sequence-3', where "N" represents completely degenerate positions in the primers. See, e.g., Sarkar et al., *PCR: Methods and Applications*, 2:318–322 (1993); and Weber et al., *Biotechniques*, 25:415–419 (1998). Thus, these primers were thirteen nucleotides long and were called double restriction site primers (DRSP) since they have restriction endonuclease recognition sequences at both ends. Four such primers were generated corresponding to the restriction endonuclease recognition sites of Cfol, Msel, AatII and BstUl (for the last two, sequences corresponding to only the four core nucleotides were used for generating the primers). A list of the DRSP primers used for SuRF is provided in Table 1.

TABLE 1

List of DRSP primers used for SuRF

| PRIMER | SEQ ID NO |
|---|---|
| 5'GAATTC NNN TCGA3' | 3 |
| 5'GAATTC NNN GCGC3' | 4 |
| 5'GAATTC NNN GGCC3' | 5 |
| 5'GAATTC NNN CCGG3' | 6 |

Example 3

Comparison of mRNA Fingerprinting Pattern by Standard ddPCR and SuRF

The fingerprinting patterns of standard ddPCR and SuRF are presented in FIG. 3. In this experiment, cDNAs from 15 µg of total RNA from FOB cells (competitor) was used to subtract from 5 µg of total RNA from MG63 cells (tester) to generate subtracted MG63 RNA. Subtracted FOB RNA was generated in the same way. Thus, in this experiment, competitor to tester RNA ratio was 3:1. A competitor to tester RNA ratio of 4:1 or 1:1 produced results very similar to that obtained with a ratio of 3:1. $T_{20}A$ and EcoR1NNNAatII primers were used in duplicate and samples from each PCR tube were loaded in duplicate on the sequencing gel. Although a large number of amplified DNA bands were observed in each case, fewer differentially expressed bands were obtained by standard ddPCR, than by SuRF. The differential display pattern of SuRF also was less complex than the standard ddPCR, and differentially expressed bands were easier to identify. Thus, subtraction of common mRNAs prior to differential fingerprinting aided in the generation of a simpler display pattern, leading to efficient identification of differentially expressed mRNAs.

A few apparently differentially expressed bands present in the standard ddPCR lanes were absent in the lanes obtained by SuRF. This could be interpreted as evidence that SuRF fails to identify some bona fide differentially expressed bands that are detectable by standard ddPCR. While such an interpretation is possible, it should be noted that bands originating from standard ddPCR have not be identified. Since standard ddPCR produces a high frequency of false positives, it cannot be concluded if those bands represent truly differentially expressed genes or are artifacts. It is also possible that a differentially expressed gene identified by one method will be missed by another method since no single method is currently available that can identify all differentially expressed genes between two samples.

General features of the sequences identified by SuRF DNA was extracted from sixty differentially expressed bands, amplified by the respective primer pairs that were used for SuRF, and 1 µL of the amplified products were cloned. Two primers were designed from the vector sequences that enabled direct amplification of the inserts from bacterial colonies. Five colonies were randomly chosen (representing each differentially expressed band) for PCR amplification of the inserts. Insert sizes after PCR-amplification were estimated by size on a 2% agarose gel. If all five colonies produced five different inserts (determined by visualization of size), each insert was sequenced. If all five looked identical in size, only two inserts were sequenced. All sequences were compared against sequence in Genbank by the computer program FastA and/or Blastsearch, using default parameters.

One hundred and five sequences were obtained after sequencing, which is more than the number of DNA bands cut out from the sequencing gels. Although care was taken to cut gel strips as thin as possible, it is unavoidable to obtain gel strips that contain more than just one sequence. Moreover, since migration of DNA on a sequencing gel is mainly governed by molecular weight, DNA segments with identical molecular weights, but a different sequence composition, can be expected to migrate as a single band. Also, >45 cycles of PCR were routinely employed to reamplify the DNA extracted from gel strips, which could allow any contaminating DNA present in a sample to be amplified. Fewer cycles of amplification disfavors amplification of contaminating DNA, but such an approach may be insufficient for producing enough DNA for cloning or other purposes. This strategy does not, in any way, affect identification of differentially expressed genes since confirmatory experiments were performed for every sequence obtained. Thus, it is not unreasonable to obtain multiple sequences from one gel strip. Differential expression of 41 sequences (out of 44) has been verified by RT-PCR with sequence-specific primers. Thus, it can be inferred that this approach identifies true, differentially expressed genes at high frequency.

With a given primer pair, approximately 200 amplified bands were obtained on the sequencing gel with conventional differential display. Assuming each of these bands originates from mRNAs from different genes, a given primer pair can be considered to have screened 200 genes for differential expression. By this estimate, ~1,600 genes have been screened for each cell type since eight different pairs of primers have been used. Thus, assuming a cell expresses ~15,000 different genes, ~10% of the expressed genes between the two cell types were screened.

In general, all differentially expressed "fat" bands on the sequencing gel (representing MG63) turned out to be mitochondrial genes, indicating a higher expression of mitochondrial genes in the osteosarcoma cell line compared to the osteoblast cell line. The general characterization of these sequences is presented in Table 2. Of the 105 sequences that were obtained, eleven were identical to known genes, three were identical to mitochondrial genes, 21 sequences had high sequence homology (70–100%) with either human and/or nonhuman genes, and 61 sequences had no sequence identity with sequences in Genbank. In addition, one sequence was obtained for 28S RNA and eight sequences representing Alu and alpha-satellite repeats were obtained.

TABLE 2

General Features of Sequences Isolated by SuRF

| | |
|---|---|
| Known genes | 11 |
| Mitochondrial genes | 3 |
| Repeat sequences | 8 |
| 28S rRNA | 1 |
| Sequences with 70–100% nucleotide identity | 21 |
| Unknown | 61 |
| Total | 105 |

It remains to be determined whether all 96 sequences (105 minus the repeat and ribosomal RNA sequences, see Table 2) that have been identified truly represent differentially expressed genes. It should be noted that none of these 96 sequences was identified more than once, indicating efficient removal of common mRNAs between the two samples. This result underscores the value of mRNA subtraction prior to display PCR. The high percentage of new sequences (61 out of 96) that resulted from this work is intriguing, and suggests that the total number of genes in the human genome is more than the present estimate of ~100,000. It is also possible that genes expressed in the musculoskeletal system is poorly represented in the public databases or that many of the identified sequences represent less abundant genes, which eluded detection by other methods. A combination of all of these possibilities probably contributed to this observation.

Example 4

Confirmation of Differential Expression of Mitochondrial Genes

Given the recent observation that mitochondrial DNA often undergoes mutation in colorectal tumors, experiments were designed to determine if the observed differential expression of mitochondrial mRNAs between FOB and MG63 cells can be further supported. Since there is very little nucleotide sequence difference between mitochondrial DNA and RNA, it is technically challenging to determine levels of mitochondrial mRNAs either by Northern blotting or by RNase protection assay (RPA), or by RT-PCR. This situation is potentially more complicated since a high level transcription of a "polycistronic" pre-mRNA is first synthesized, which is then cleaved to produce mature mitochondrial mRNAs. Thus, conventional RT-PCR or RPA cannot distinguish between the pre-mRNA and mature mRNAs. A novel RT-PCR strategy has been developed to determine relative level of mitochondrial mature mRNAs.

Levels of cytochrome oxidase II (coxII) and cytochrome oxidase b (cytb) mRNAs relative to the expression of GAPDH mRNA (a nuclear coded cytoplasmic mRNA) were determined by RT-PCR. Since both of these cell lines are of osteoblastic lineage, most or all of the genes in these cell lines that are not associated with tumor phenotype should have similar levels of mRNA expression. Primers intended to specifically interact with mitochondrial mRNA were made consisting of 22 "T" nucleotides at the 5' end, followed by 3–5 mRNA-specific sequences at the 3' end. These primers should support DNA synthesis from a template having poly A sequence preceded by the cognate complimentary sequence. Therefore, these primers should be specific only for poly A+RNA and should not anneal and/or support DNA synthesis from mitochondrial pre-mRNA or mitochondrial DNA, sequences since they lack polyA stretches. The other primer (sense primer) used was not discriminatory between mitochondrial DNA, pre-mRNA, or matured RNA sequences. Verification of this approach was obtained by amplifying a 3' segment of an mRNA and demonstrating the poly A junction sequence by direct sequencing of the amplified product.

An amplified segment of 300 bp was expected from GAPDH mRNA and amplified DNAs of 417 bp and 258 bp were expected for cox II and cyt b mRNAs, respectively. Higher levels (~2-fold) of both mRNAs (cox II and cyt b) were observed in MG63 cells compared to FOB cells. The amplified band representing GAPDH mRNAs was nearly invisible in MG63 samples, indicating greater expression of these mRNAs in MG63 cells.

Example 5

Confirmation of Differential Expression of Lysyl Oxidase, FC68, and FM94 mRNAs

Expression of other mRNAs that appeared to be expressed more in MG63 compared to FOB cells was evaluated. Again, RT-PCR in the presence of GAPDH primers was performed to determine relative level of expression. Three different mRNAs- lysyl oxidase, and two uncharacterized genes (FC68 and FM94) were amplified. Predicted products of 320 bp, 204 bp, 196 bp, and 162 bp were expected for GADPH, lysyl oxidase, FC68, and FM94 mRNAs, respectively. In all cases, identification of the amplification products was confirmed by direct automated sequencing. All of these three different mRNAs appear to express more in MG63 cells compared to FOB cells. Primers for FC68 and FM94 did not produce any amplified bands from genomic DNA.

For reasons of ease, 35 cycles of PCR were performed for relative quantification of all the mRNAs presented in the above experiments. For many reactions, 35 cycles of amplification might represent a stage beyond the ideal range of exponential amplification. The relative difference in the amount of two amplicons amplifying in a PCR tube is expected to go down if PCR is carried out beyond the exponential phage of amplification. The fact that an upregulation of the respective mRNAs was observed even after 35 cycles of PCR, however, indicates that the actual differences in expression level of these mRNAs between FOB and MG63 cells might be greater than observed.

A visual comparison of the intensity of the amplified GAPDH product indicates that the PCR efficiency between these experiments may be varied without being limited to a particular mechanism, differences in PCR amplification may be due to competition between the two templates for many factors that determine the final outcome of amplification of each of the templates. One significant factor is the relative abundance of the templates in a sample. Copy number of a mitochondrial transcript usually is very high, since there are ~1000 copies of mitochondria/cell, and each mitochondrion may have one or more copies of DNA that can produce many copies of mitochondrial mRNA transcripts. Thus, the copy number of both the coxII and cyt b mRNAs probably is much higher than that for GAPDH mRNA. In the experiment with mitochondrial mRNAs, weak amplification of GAPDH mRNA relative to the two mitochondrial mRNAs was observed, while in the experiment without mitochondrial mRNAs, amplification of GAPDH mRNA was relatively higher than the test mRNAs. Results obtained from repeat experiments support this explanation.

Example 6

Preferred Amplification of Coding Sequences (PACS)

To assess the ratio of coding versus non-coding sequences, the lengths of coding and 3' non-coding sequences from eight human genes (Table 3) were manually estimated. The mRNA sequences were randomly chosen, except with a condition that the ends of the 3' non-coding sequences have to be either defined or can be predicted. The total coding sequence of these eight mRNAs was 15,027 nucleotides, whereas the total non-coding sequence was 7,199 nucleotides, resulting in a ratio of coding versus non-coding sequence of approximately 2:1. Assuming this ratio reflects the distribution of coding and 3' non-coding sequences in general, coding sequences can be preferentially acquired with a non-poly A tail based primer.

TABLE 3

Size Distribution of Coding and 3'-Non-Coding Sequences of Human mRNAs

| Number | mRNA | Coding | 3' Non-coding |
|---|---|---|---|
| 1 | beta-action | 1,504 nucleotides | 649 nucleotides |
| 2 | TGF-β1 | 1,510 nucleotides | 721 nucleotides |
| 3 | LRP[a] | 866 nucleotides | 149 nucleotides |
| 4 | P130 | 2,099 nucleotides | 347 nucleotides |
| 5 | RBL2[b] | 3,938 nucleotides | 1,525 nucleotides |
| 6 | Calumein | 947 nucleotides | 2,308 nucleotides |
| 7 | RBP[c] | 1,277 nucleotides | 951 nucleotides |
| 8 | EXPR[d] | 2,888 nucleotides | 549 nucleotides |
| Total | | 15,027 nucleotides | 7,199 nucleotides |

[a]LRP = Lysine rich protein; [b]RBL2 = Retinoblastoma-Like Protein; [c]RBP = Retinoblastoma binding protein; [d]EXPR = Exportin Four initiation primers were generated whose general sequence was: 5' BamH1 restriction enzyme site—NNN-ATGX3' (where "N" represents a completely degenerate position and "X" is either A, T, G, or C). For example, the nucleotide sequence of one such primer was 5'GGATC-CNNNATGA3' (SEQ ID NO:7). The last nucleotide (either A, T, G, or C) should increase specificity of the primer by allowing DNA synthesis only from appropriate sequence contexts in an mRNA. All these primers have seven 3'-nucleotides to completely match with a template (such as NNNATGA3'). The restriction enzyme sequence at the 5' and has been appended to facilitate cloning of the amplified DNA, if necessary. The other primers were DRSPs, as described above. Four such primers were designed based on the recognition sequences of Cfol, MseI, AatII and BstUI enzymes (for the last two, only the four core nucleotides were used). The general structure of these primers were: 5'GAATTCNNNGGCC3' (SEQ ID NO:5) (for a HaeIII restriction site-based primer). As with the initiation primer, the restriction enzyme sequence at the 5' end can be used to facilitate cloning. For each PCR, an initiation primer and a DRSP were used. Table 4 contains a list of primers used.

TABLE 4

List of primers used for PACS

| | SEQ ID NO |
|---|---|
| Initiation primers | |
| 5'GGATCC NNN ATGA3' | 7 |
| 5'GGATCC NNN ATGT3' | 8 |
| 5'GGATCC NNNATGG3' | 9 |
| 5'GGATCC NNN ATGC3' | 10 |
| DRSPs | |
| 5'GAATTC NNN TCGA3' | 3 |
| 5'GAATTC NNN GCGC3' | 4 |
| 5'GAATTC NNN GGCC3' | 5 |
| 5'GAATTC NNN CCGG3 | 6 |

PACS between FOB and MG63 cell mRNAs: A representative differential mRNA display pattern between FOB and MG63 cells obtained by PACS is presented in FIG. 4. PCR for each sample was carried out in duplicate and each of those samples were electrophoresed in triplicate. As can be observed in FIG. 4, differentially amplified bands are clearly identifiable. Using cDNA from a variety of sources, including other cell lines derived from osteogenic sarcoma, Ewing's tumor, and brain tumor samples, PACS has been performed >200 times and has consistently produced desired results. Since smaller DNA bands were not included for further analysis, differentially expressed DNA bands were examined in the upper portion of the gel that roughly contains about 125 bands. If each of these bands represent different mRNA species, then that would imply screening of 125 different mRNA species with one pair of primers. Sixteen different combinations of primers have been used, which is equivalent to screening 4,000 different mRNAs (2,000 each for FOB and MG63 cells) and equivalent to about 15% of all the expressed genes in each of these two cell types (assuming a cell expresses ~15000 genes). Since redundant sequences were identified at a very low frequency (<1%), the estimate presented above should be realistic.

Example 7

General Characteristics of the CSTs Obtained by PACS

The general characteristics of the differentially expressed sequences identified by PACS are presented in Table 5. In total, 103 sequences were obtained. Of them, two were cloning vector sequences (category 7) and five were repeated sequences belonging to satellite and L1 repeats (category 8). More than 95% of the sequences contained the 'ATG' triplet sequence, indicating that primers directed to the 'ATG' sequence indeed recognized them. Twenty-seven sequences matched with known mRNA coding regions (category 1), whereas only two sequences matched with known 3'-end non-coding regions (category 2). This observation strongly supports the estimate that coding sequences are more abundant than 3' non-coding sequences (in human mRNAs) and that, given such a distribution pattern, PACS will preferentially identify coding versus non-coding sequences. Twenty-one sequences (category 3) had moderately high homology (60–95%) with uncharacterized human sequences, and in addition had high homology (60–80%) with bacterial, yeast, C. elegans, or plant sequences. These sequences may belong to transcribed genes; therefore, these sequences have been listed under the category of "suspected genes". If these sequences are assumed to represent coding region of mRNAs, then PACS can be considered a robust technique for the acquisition of CSTs. Six sequences (category 4) had greater than 80% sequence identity with human sequences, although the potential nature of these sequences could not be determined. In addition, there were twenty sequences having 60–80% sequence identity with human sequences (category 5), but lacking any notable sequence identity with other organisms. Finally, there were twenty sequences having little or no homology (0–60%) with sequences in Genbank (category 6). Interestingly, ribosomal RNAs were not identified, illustrating the fact that amplified DNA bands representing common mRNAs between FOB and MG63 samples were not picked up for further analyses. Taken together, these observations indicate that the method identifies an overwhelming majority of coding sequences over non-coding sequences.

TABLE 5

General Characteristics of Sequences Obtained by PACS Between FOB and MG63 Cells

| Category | Sequence Type | # of Sequences |
| --- | --- | --- |
| 1 | Known genes | 27 |
| 2 | 3' Untranslated sequences | 2 |
| 3 | Suspected genes | 21 |
| 4 | >80% sequence identity with human sequence in Genebank | 6 |
| 5 | 60–80% sequence identity with human sequence in Genebank | 20 |
| 6 | <60% sequence identity with human sequence in Genebank | 20 |
| 7 | Cloning vector sequences | 2 |
| 8 | Repeat sequences | 5 |
|  | Total | 103 |

Example 8

Expression Profile of a Set of Genes/coding Sequence Tags (CSTs) Identified by PACS Expression of mitochondrial mRNA between FOB and MG63 cells were examined. The level of expression of ATPase 6 mRNA (a segment of which was identified by PACS analysis) was evaluated by RT-PCR. cDNAs from FOB and MG63 cells were used for PCR with primers to amplify segments from beta-actin and ATPase 6 mRNAs. Thirty-five cycles of PCR were carried out at 94° C. for 1 min, 50° C. for 1 min, and 72° C. for 1 min after which 5µL of the PCR products were electrophoresed on a 2% agarose gel, which then was stained with ethidium bromide. The upper band (502 bp) indicates an amplified segment for actin mRNA, the lower band (309 bp) indicates amplified segment for ATPase 6 mRNA. PCRs were done in duplicate. Authenticity of the amplification products were confirmed by direct sequencing. Two- to three-fold higher level of ATPase mRNAs were present in the tumor cell line compared to the osteoblasts.

Clones FM62, FM80, FM87, FM141, FC30, FC38, FC89, SP100 and Cox II (cytochrome oxidase II) were used as probes in Northern blots using total RNAs from FOB and MG63 cells. FM62 has 80% identity with an uncharacterized human sequence; FM80 has no match with sequences in Genbank; FC89 has 70% sequence identity with human HPRT mRNA; and FC30 and FM87 have 69% and 60% identity, respectively, with uncharacterized human sequences. SP100 has 100% sequence identity with human SP100 mRNA. Thus, except for SP100 and CoxII, there is no information whether these sequences actually represent expressed mRNA sequences.

Northern blots of total RNAs from FOB and MG63 cells were prepared and hybridized with radioactive probes, specific primers were generated from each of the above sequences and probes were made by PCR. These results establish two important observations: (1) That these probes represent expressed genes, and (2) The mRNAs are differentially expressed between the two cell types such that FC38, SP100, and CoxII are expressed more in MG63 cells, whereas FM62, FM80, FC89, FC30, and FM87 are expressed more in FOB cells compared to their expression in MG63 cells.

Level of expression of another clone termed RBL (for retinoblastoma-like) was also compared between the two cell types. RBL is 100% identical to P130 mRNA sequences that are known to form complexes with the adenovirus E1A protein. See, Li et al., *Genes Dev.*, 7:2366–2377 (1993). Expression of RBL mRNA was evaluated by RT-PCR. Co-amplification of desired segments of β-actin and RBL mRNAs with gene-specific primers were carried out in duplicate using cDNAs from FOB and MG63 cells. The level of RBL mRNA expression was elevated in MG63 cells compared to its expression in FOB cells. Thus, using Northern blotting and RT-PCR, differential mRNA expression corresponding to eleven CSTs/genes, has been demonstrated.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of amplifying nucleic acid sequences, said method comprising amplifying a population of cDNA molecules using a plurality of different nucleic acid primer pairs, each said pair consisting of nucleic acid primers 10 to 40 nucleotides in length, wherein said plurality of different nucleic acid primer pairs comprises at least four different initiation primers, wherein said at least four different initiation primers have the sequences 5'-R-S-ATG-A-3', 5'-R-S-ATG-C-3', 5'-R-S -ATG-G-3', and 5'-R-S-ATG-T-3', where R represents a restriction endonuclease recognition sequence, and S represents a degenerate nucleotide sequence from 1 to 10 nucleotides in length, and wherein a second nucleic acid primer of said primer pair comprises two restriction endonuclease recognition sequences.

2. The method of claim 1, wherein said population of cDNA molecules is from a biological sample.

3. The method of claim 1, wherein said population of cDNA molecules is from a tissue sample.

4. The method of claim 1, wherein said population of cDNA molecules is from prokaryotic cells.

5. The method of claim 1, wherein said population of cDNA molecules is from eukaryotic cells.

6. The method of claim 1, wherein said population of cDNA molecules is from neoplastic cells.

7. The method of claim 1, wherein said population of cDNA molecules is amplified using at least 16 nucleic acid primer pairs.

8. A composition comprising at least four different nucleic acid molecules, wherein each said nucleic acid molecule is 10 to 40 nucleotides in length, and wherein said at least four different nucleic acid molecules have the sequences 5'-R-S -ATG-A-3', 5'-R-S-ATG-C-3', 5'-R-S-ATG-G-3', and 5'-R-S-ATG-T-3', where R represents a restriction endonuclease recognition sequence, and S represents a degenerate nucleotide sequence from 1 to 10 nucleotides in length.

9. A kit comprising at least four different initiation nucleic acid primers and a double restriction site nucleic acid primer, wherein each said primer is 10 to 40 nucleotides in length, wherein said at least four different initiation nucleic acid primers have the sequences 5'-R-S-ATG-A-3', 5'-R-S-ATG-C-3', 5'-R-S-ATG-G-3', and 5'-R-S-ATG-T-3', where R represents a restriction endonuclease recognition sequence, and S represents a degenerate nucleotide sequence from 1 to 10 nucleotides in length, and wherein said double restriction site nucleic acid primer comprises two restriction endonuclease recognition sequences.

10. The kit of claim 9, said kit comprising at least sixteen different initiation nucleic acid primers.

11. The kit of claim 9, said kit further comprising a plurality of different double restriction-site nucleic acid primers, wherein each said double restriction site nucleic acid primer comprises two restriction endonuclease recognition sequence.

12. The kit of claim 11, said kit comprising at least four different double-restriction-site nucleic acid primers.

13. The kit of claim 11, said kit comprising at least sixteen different double restriction-site nucleic acid primers.

14. The kit of claim 9, said kit further comprising a sorting element.

15. The kit of claim 14, wherein said sorting element is an oligo-dT magnetic bead.

16. The kit of claim 14, wherein said sorting element is an oligo-dT biotin molecule.

17. The kit of claim 14, wherein said sorting element is an oligo-dT cellulose molecule.

18. A method of identifying differentially expressed mRNA molecules, said method comprising hybridizing a population of mRNA-derived cDNA molecules from a first sample to a population of RNA molecules from a second sample; converting unhybridized, differentially expressed RNA molecules to subtracted cDNA molecules; and identifying said subtracted cDNA molecules by amplifying said subtracted cDNA molecules using a plurality of different primer pairs, each said primer pair comprising an initiation nucleic acid primer and a double restriction site primer, wherein said plurality of different nucleic acid primer pairs comprise at least four different initiation primers, wherein said at least four different initiation nucleic acid primers have the sequences 5'-R-S-ATG-A-3', 5'-R-S-ATG-C-3', 5'-R-S-ATG-G-3', and 5'-R-S-ATG-T-3', where R represents a restriction endonuclease recognition sequence, and S represents a degenerate nucleotide sequence from 1 to 10 nucleotides in length, and wherein said double restriction site nucleic acid primer comprises two restriction endonuclease recognition sequences, wherein said subtracted cDNA molecules correspond to differentially expressed mRNA molecules.

19. The method of claim 18, wherein said identifying step further comprises sequencing said amplified cDNA molecules.

20. The method of claim 18, wherein said amplified cDNA molecules are detectably labeled.

21. The method of claim 20, wherein said detectable label is a radioisotope or a non-radioactive label.

22. The method of claim 21, wherein said non-radioactive label is a fluorescent moiety.

23. The method of claim 18, wherein a non-radioactive dye is used to detect said amplified cDNA molecules.

* * * * *